(12) United States Patent
Burgard (10) Patent No.: US 6,419,683 B1
(45) Date of Patent: Jul. 16, 2002

(54) INSTRUMENT FOR RESECTIONING HEMORRHOIDS

(76) Inventor: Gunther Burgard, Fasanenweg 7, D-66424 Homburg (DE)

( * ) Notice: Subject to any disclaimer, the term of this patent is extended or adjusted under 35 U.S.C. 154(b) by 0 days.

(21) Appl. No.: 09/423,189

(22) PCT Filed: Apr. 23, 1998

(86) PCT No.: PCT/EP98/02423

§ 371 (c)(1),
(2), (4) Date: Feb. 28, 2000

(87) PCT Pub. No.: WO98/49950

PCT Pub. Date: Nov. 12, 1998

(30) Foreign Application Priority Data

May 2, 1997 (DE) .......................... 197 18 708

(51) Int. Cl.[7] ............................................. A61B 17/32
(52) U.S. Cl. ........................................ 606/169; 606/28
(58) Field of Search .................. 606/170, 169, 606/27, 28, 32, 50, 31, 107; 604/22

(56) References Cited

U.S. PATENT DOCUMENTS

| | | | | |
|---|---|---|---|---|
| 4,765,331 A | * | 8/1988 | Petruzzi et al. | 606/32 |
| 4,869,715 A | * | 9/1989 | Sherburne | 606/107 |
| 6,033,397 A | * | 3/2000 | Laufer et al. | 606/27 |

* cited by examiner

*Primary Examiner*—Kevin T. Truong
(74) *Attorney, Agent, or Firm*—Michael J. Donohue; Seed IP Law Group, PLLC (57) ABSTRACT

The present invention relates to an instrument for resectioning hemorrhoids for the minimal invasive subanodermal removal of hemorrhoidal tissue. In order to reduce surgical intervention to an absolute minimum and to subject a patient suffering from hemorrhoids to an operation which is as gentle as possible, the invention provides for an instrument for resectioning hemorrhoids, comprising a narrow, elongated carrier device, a vibrating surgical device which reduces the size of tissue so that hemorrhoidal tissue can be prepared and fragmented, and at least one milling unit for removing said tissue.

45 Claims, 8 Drawing Sheets

INSTRUMENT FOR RESECTIONING HEMORRHOIDS

The present invention relates to an instrument for resectioning hemorrhoids for the minimal invasive subanodermal removal of hemorrhoidal tissue.

Hemorrhoidal ailments account for the most frequent rectal disease found in the Western civilized world; the disease frequency is said to be 50% among the population over 50 years. Hemorrhoids are vessel convolutes covered with mucous membrane, which are noticed by bleeding, pressure sensation or protrusion. Starting from a hemorrhoidal enlargement of the third and fourth degree, a surgical intervention in which tissue is removed manually is required for providing relief.

As a rule, hemorrhoidal tissue is formed below the anoderm, i.e. below the transitional skin which is located at the end of the anal canal between the mucous membrane of the rectum and the external skin of the buttock. The anoderm has an extremely high nerve density which ensures sensory continence, i.e. the ability to distinguish gas, liquid or feces and to retain the same.

The methods which have so far been known are concerned with segmental excisions, e.g. according to Milligan-Morgan, in which large incisions are required in the highly sensitive anoderm. This may impair the sensory system of the anoderm and is relatively painful for the patient in the subsequent wound healing process.

U.S. Pat. No. 4,428,748 describes an ophthalmic surgical instrument for treating cataracts of the crystalline lens. The operative attachment of the instrument is needle-shaped and is provided in the area of the tip with a milling opening for removing tissue parts in the area of the crystalline lens. The outer part of the needle can be driven in an ultrasonic surgical manner. For the selective removal of portions of the crystalline lens the needle-like lens is required for selectively treating the parts to be removed within the millimeter range. The instrument is not suited for treating inhomogeneous tissue structures.

EP 0 591 619 A1 discloses a resectioning instrument for the operative removal of tumors, or the like, for instance in the field of gallbladders. An ultrasonic unit is used for reducing the size of the tumor employing an endoscope. The size-reduced tumor particles are removed with the help of a flushing device.

U.S. Pat. No. 4,931,047 suggests an ultrasonic unit for the fragmentation of tumor tissue on the digestive organ. The tissue is fragmented by way of ultrasound to eliminate the tumor.

(Continued on page 2 of the original description)

U.S. Pat. No. 3,945,375 and U.S. Pat. No. 3,937,222 disclose surgical milling units for the removal of tissue. Each milling unit comprises at least one rotating knife which is rotating in the area of an opening of a sleeve, so that tissue within the area of the opening can be removed by the milling device.

It is the object of the present invention to provide an instrument permitting a simple and gentle surgical removal of hemorrhoidal tissue in accordance with anatomical conditions.

This object is achieved according to the invention by a resectioning instrument for the minimal invasive, subanodermal, submucous removal of hemorrhoidal tissue, with a narrow, elongated carrier device being provided, comprising a vibrating surgical tissue size-reducing device and at least one tissue-removing milling unit.

Only a small incision in the skin is required for the surgical application of said instrument. The incision is preferably made at the base of a hemorrhoidal node on the anal edge region. The anoderm ends in this region or passes into the skin of the buttock. The anoderm is here not incised or only incised to a very slight degree.

Thanks to the small incision, the narrow, elongated carrier device can be introduced below the anoderm. In the subanodermal region the removal of the hemorrhoidal plexus may be started on the front end portion of the instrument.

With the tissue size-reducing device, the hemorrhoidal tissue can be prepared and fragmented in a vibrating surgical manner. It can be isolated from the inner sphincter at the one side and from the anoderm at the other side. The anoderm remains intact and the Musculus internus undamaged.

An ultrasonic surgical tool may e.g. be used as the vibrating surgical device which is e.g. operated within the range of 20,000 to 40,000 Hz. The hemorrhoidal tissue can thus be prepared and fragmented in a very selective manner and without any damage to the healthy tissue.

The prepared tissue can then be reduced in size and removed with the tissue-removing milling unit, so that it is removable piece by piece from the area between the sphincter and the anoderm.

This instrument allows for a very easy operation which does not require any assistance and only needs about a third of the time of conventional surgical methods.

The highly sensitive anoderm remains intact and can subsequently be repositioned into the anal canal in accordance with the anatomy. This means for the patient that less healthy tissue is destroyed, resulting in a faster wound healing process. Because of the maintained anoderm the postoperative wound pain is considerably reduced.

Preferably, when viewed in the longitudinal direction of the carrier device, the tissue size-reducing device can be arranged closer to the tip of the carrier device than the milling unit. As a result, when the instrument is advanced into the hemorrhoidal tissue, the tissue sizereducing device will first get into active contact with the tissue. Preparation and fragmentation will be performed in the advance direction before the milling unit becomes operative.

The tissue size-reducing device can be arranged in a particularly advantageous manner directly at the foremost tip of the carrier device. Thus the preparation can be performed at the foremost end of the carrier device, so that the preparation can be carried out during the selective advance movement of the instrument.

Advantageously, the milling device can be arranged in spaced-apart relationship with the tip of the carrier device in the lateral circumferential area of the carrier device. As a consequence, the milling unit can be operated laterally and, when viewed in the advance direction, will only become active after the hemorrhoidal tissue has been prepared.

Specifically, at least two spaced-apart milling openings of the milling unit may be provided in the lateral circumferential area of the carrier device. Tissue can there by be removed at two sides, so that the hemorrhoidal tissue can be removed relatively rapidly and in different spatial directions.

When viewed in a direction perpendicular to the longitudinal direction, the milling openings should be arranged approximately on the same circumferential line. This ensures that during the advance movement of the instrument the milling action will only begin from a specific circumferential line onwards.

In a preferred embodiment the front end portion may comprise an inclined surface extending at an angle relative to the longitudinal axis of the carrier device, resulting in the formation of a front end portion having an approximately wedge-shaped or beak-shaped cross-section. Such a shape facilitates the advance movement of the instrument in the tissue.

In a particularly advantageous manner, the angle of inclination of the inclined surface may be about 40° to 50°, preferably 45°, relative to the longitudinal axis of the carrier device. With such an angle, the front end portion is still sufficiently stable and can be advanced relatively easily into the hemorrhoidal tissue.

In a variant of the invention an active surface of the tissue size-reducing device may be integrated at least in part into the inclined surface. As a result, the tissue size-reducing operation can be performed in a direction arranged at a slight angle relative to the advance direction, so that a slightly lateral preparation is also possible.

A light providing device which emits diaphanoscopically usable light is possibly provided on the front end portion. Diaphanoscopy means the transillumination of body parts to detect the structure or contours of tissue by way of shadows. During use of the instrument the surgeon can detect the structure of the hemorrhoidal tissue and its boundaries as well as surrounding tissue and he can selectively push the instrument to the desired place. He will recognize diseased tissue as compared with healthy tissue and detect the position of the front end of the instrument to guide the instrument in a purposeful manner to the desired places. During the process he is looking through the anoderm.

The light providing device may e.g. be an optical-fiber light guide leading to the front end portion and emitting cold light.

Preferably the light providing device may e.g. be arranged in the surface area between the tissue size-reducing device and the milling unit(s). The active surface o f the tissue size-reducing device and the milling unit, respectively, is thereby illuminated and can be seen by the surgeon through the tissue whereby he can control the instrument in a selective manner.

In particular, the light providing device may be disposed in an inclined surface extending at an angle relative to the longitudinal axis of the carrier device. This permits an approximately obliquely bent light emission so that the laterally surrounding area around the front end portion is illuminated in an improved manner and can be seen in a diaphanoscopically improved way.

Possibly, the light providing device is disposed in the circumferential area near the milling unit. As a result, the work portion treated with the milling unit can be illuminated and seen in a particularly clear manner.

The light providing device should have a large-surface light-emitting area relative to the active surfaces of milling unit and/or issue size-reducing device. This ensures a particularly clear illumination of the hemorrhoidal tissue to be treated.

It is particularly advantageous when the carrier device comprises at least one suction channel which is connectable to a vacuum pump and terminates in a suction opening provided on the front end portion. With the help of the suction opening it is possible to produce a slight negative pressure in the front portion so that surrounding tissue is slightly pulled towards the front end portion. This establishes a contact with the vibrating surgical tissue size-reducing device, and the tissue to be removed is supplied to the milling unit.

In a variant of the invention, the suction opening may be centrally provided in an active surface of the tissue size-reducing device. As a result, the surrounding tissue is guided in a relatively selective manner to the active surface, so that the tissue will be reduced in size upon contact.

It is possible to design a milling opening/milling openings as a suction opening in the circumferential area of the carrier device, with a milling knife which is movable in the carrier device being provided in the area thereof. As a result, hemorrhoidal tissue is pulled towards the milling knife because of a small negative pressure.

In a preferred embodiment the carrier device may comprise at least one flushing channel which is connectable to a flushing system and terminates in a flushing opening provided in the front end portion. Flushing liquid can be supplied or discharged via the flushing opening. As a result, the area below the anoderm can be flushed, and possibly free tissue parts can be detached. The flushing liquid may either flow back through a flushing channel of the instrument or exit at the incision site between skin and instrument. The suction channel may also be used for returning flushing liquid. In principle, the same channel may be used as suction channel and flushing channel by successively alternating the direction of flow therethrough.

It is also possible to design a milling opening as a flushing opening in the circumferential area of the carrier device, with the milling knife which is movable in the carrier device being provided in the area thereof. As a result, the flushing liquid can also be used for cleaning the milling unit, for instance in cases where the latter threatens to be clogged by tissue parts. Furthermore, tissue parts can be flushed away through the milling opening. Optionally, the flushing system may also serve to cool the vibrating unit.

Preferably, the flushing opening may be provided centrally in an active surface of the tissue size-reducing device.

Particularly, the carrier device may comprise a first part carrying the front end portion and a second part which is detachably connectable to the first part and designed as a handle.

In a further development of the invention the handle may comprise a marking indicative of the angular orientation of the front end portion relative to the longitudinal axis of the carrier device. With the help of the marking it is possible to detect the rotational position of the front end portion on the externally accessible handle so that the exact position of the tissue size-reducing device and the milling unit, respectively, can be made out.

The milling unit is possibly provided with a milling knife which is movable in the carrier device and arranged in the area of a milling opening of the carrier device. The milling knife can e.g. rotate in the carrier device, with the knife being provided in the area of the milling opening. Tissue which is positioned inside the area of the milling opening is cut by the milling knife in metered amounts and removed. Thanks to the arrangement of the milling knife within the carrier device, the milling knife can be introduced into the tissue in a relatively protected manner and moved therein. Tissue is only removed in the area of the milling opening. A milling unit of such a configuration may also be designated as a "shaver".

According to a preferred embodiment the tissue size-reducing device and/or the milling unit can be supported in the carrier device in a longitudinally displaceable manner. The tissue size-reducing device can thereby be advanced in a selective manner to the tumor parts to be treated. The carrier device may e.g. be designed as a sleeve or trocar in which the tissue size-reducing device can be manually introduced from behind and slid beyond the front end of the trocar.

Preferably, the active surface of the tissue size-reducing device can be pushed out of the carrier device into a position in which the active surface projects forwards from the carrier device. Thus the active surface can serve as the foremost tip which advances in the tissue portion by portion and provides room for the trailing carrier device. As a result, the active surface is not automatically fixed to the shape of the front end portion of the carrier device, but can project separately, e.g. in the form of a finger, from the carrier device.

Particularly, the active surface of the tissue reducing device may have an approximately oval or circular shape.

Embodiments of the present invention are shown in the drawings and will be described in the following.

Figure 1:
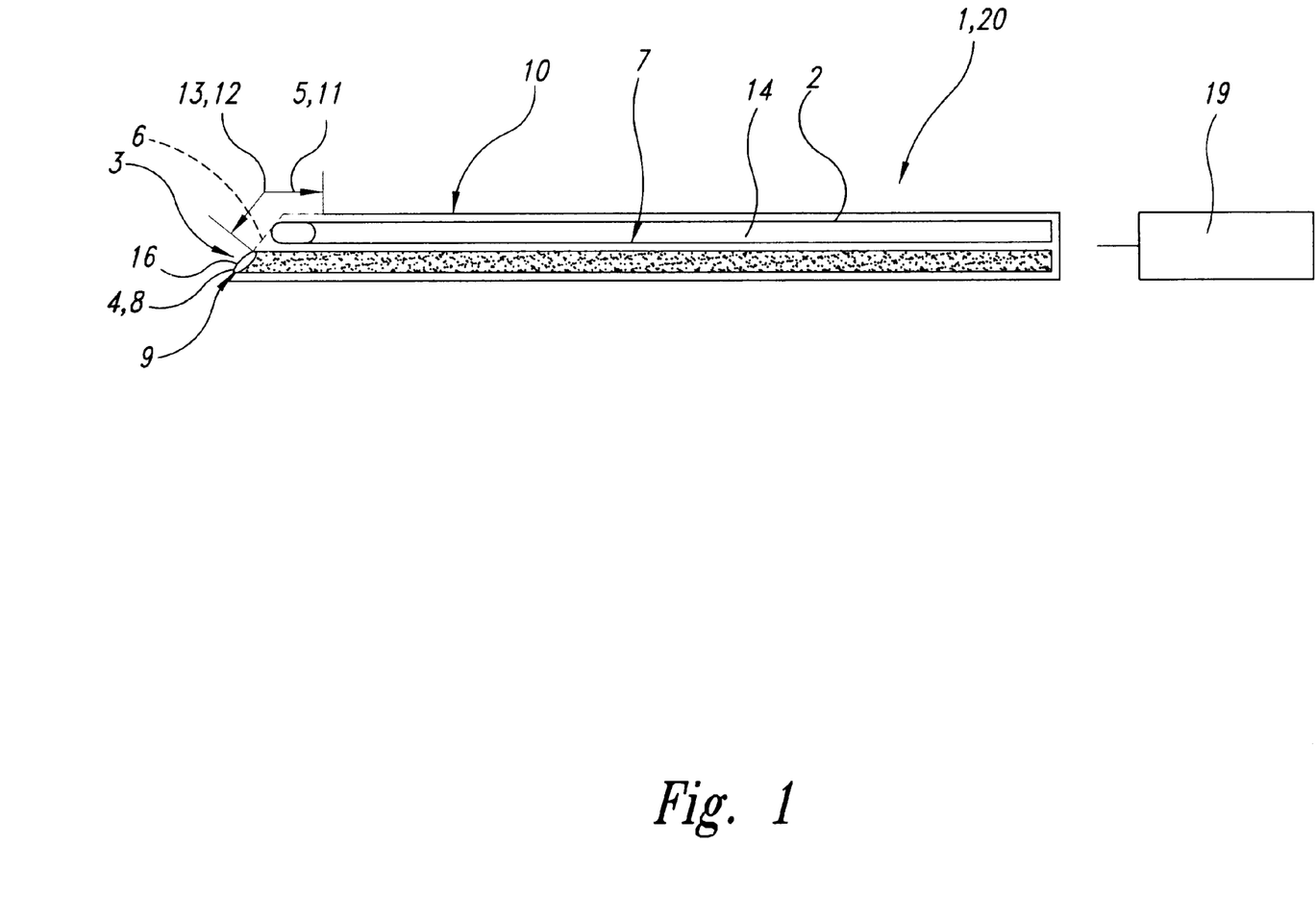
FIG. 1 is a schematic lateral view showing a first part of an instrument of the invention according to a first embodiment of the invention.

FIG. 1 schematically shows a first part 20 of a hemorrhoid resectioning instrument 1 of the invention in accordance with a first embodiment. Part 20 comprises a narrow, elongated carrier device 2 of an approximately oval cross-section. The cross section is relatively small; it may be about 0.5 cm.

The first part 20 is approximately finger-shaped having a length of about 7 cm. The carrier device 2 has a front end 3 with a tissue size-reducing device 4 and a tissue-removing milling unit 5 provided thereon.

The front end portion has an inclined surface 6 which extends at an angle of about 45° relative to the longitudinal axis 7 of the carrier device. In the illustrated view the front end portion 3 has an approximately wedge-shaped cross-section.

An active surface 8 of the tissue size-reducing device 4 is integrated into the inclined surface 6. The active surface 8 has a titanium surface which can be vibrated so that it will reduce the size of adjacent tissue in a vibrating surgical manner. The vibration is preferably of an ultrasonic surgical type having a frequency range of about 20,000 to 40,000 Hz. Such vibrations are e.g. produced by piezoelectric materials which are subjected to mechanical vibration by alternating voltage and induce the titanium surface to vibrate.

The active surface 8 is directly located on the foremost tip 9 of the carrier device 2. When viewed in the longitudinal direction of the carrier device, it is positioned closer to the tip 9 than the milling unit 5.

The milling unit 5 is spaced apart from the tip of the carrier device 2. It comprises a milling opening 11 provided in the lateral circumferential area 10. The carrier device has disposed therein a rotating milling knife (not shown) which is rotating in the area of the milling opening 11 so that tissue can be removed by the milling knife through the milling opening 11.

A drive shaft (not shown) for the milling knife extends longitudinally through the carrier device 2 up to a corresponding external device. Likewise, the drive mechanism for vibrating the tissue size-reducing device 4 extends longitudinally through the carrier device 2 to a corresponding peripheral unit.

Figure 2:
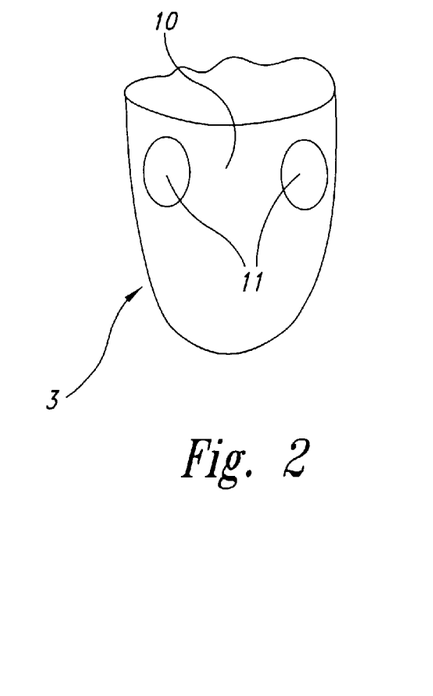
FIG. 2 is a schematic diagram showing the arrangement of two milling openings at the front end portion of an instrument of the invention according to the first embodiment.

FIG. 2 schematically shows the circumferential area 10 of the front end portion 3 with two milling openings 11. The two milling openings 11 can optionally be served by the same rotating knife, whereby two spaced-apart milling units 5 are formed in principle. The milling openings 11 are positioned approximately on the same circumferential line in a direction perpendicular to the longitudinal axis of the carrier device 2 and are spaced apart from each other. The milling openings are spaced apart from the inclined surface 6 or just abut on said surface.

When seen in a vertical cross-sectional view relative to the longitudinal axis, the outer circumferential area 10 may be without any milling openings over a circumferential angle of about 100° to 120° so as not to destroy tissue within said area.

Figure 3:
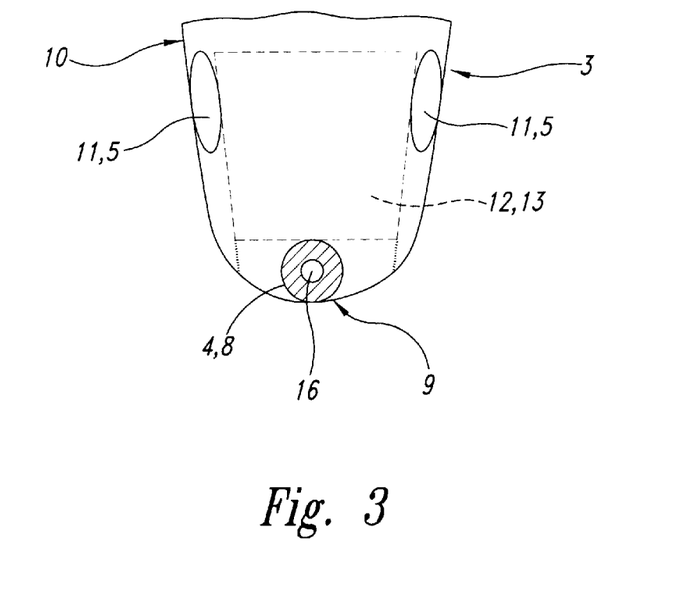
FIG. 3 is a schematic diagram showing the arrangement of the individual elements of the front end portion of an instrument of the invention according to the first embodiment.

As shown in FIGS. 1 and 3, a light providing device 12 is disposed on the front end portion. The device emits light which can be used for diaphanoscopic observations. Diaphanoscopy means the transillumination of tissue parts where different tissue portions can be seen as shadows from the outside through the tissue.

The light used may be cold light which is transmitted through a glass-fiber cable extending along the carrier device 2.

FIG. 1 shows by way of a dotted line a light-providing surface area 13 which in comparison with the milling openings 11 and the active surface 8 is designed as a large surface. The surface area 13 is partly provided in the inclined surface 6 and, in cohering fashion therewith, partly in the circumferential area 10.

FIG. 3 is a schematic straight top view on the inclined surface 6. The surface area 13 is provided in the inclined surface 6. A milling opening 11 is provided at each side in the laterally rounded circumferential area 10. The active surface 8 of the tissue size-reducing device 4 is positioned at the tip 9. The light-providing surface area 13 is approximately arranged between the active surface 8 and the milling openings 11.

The milling openings 11 are connected to a suction channel 14 which extends in longitudinal direction through the carrier device 2 and is connectable to a suction pump. Thus the milling opening serves as a suction opening.

As shown in FIGS. 1 and 3, a suction opening 15 which is also connectable via a suction channel to the suction pump is centrally positioned in the active surface.

The suction opening 16 and the milling opening 11 can optionally be used as a flushing opening, the corresponding suction channel being then usable as a flushing channel. A plurality of separate flushing channels may optionally be provided for, so that flushing fluid can e.g. be ejected through the milling opening 11 and the flushing fluid can again be sucked in through the suction opening 16, or vice versa.

Figure 4:
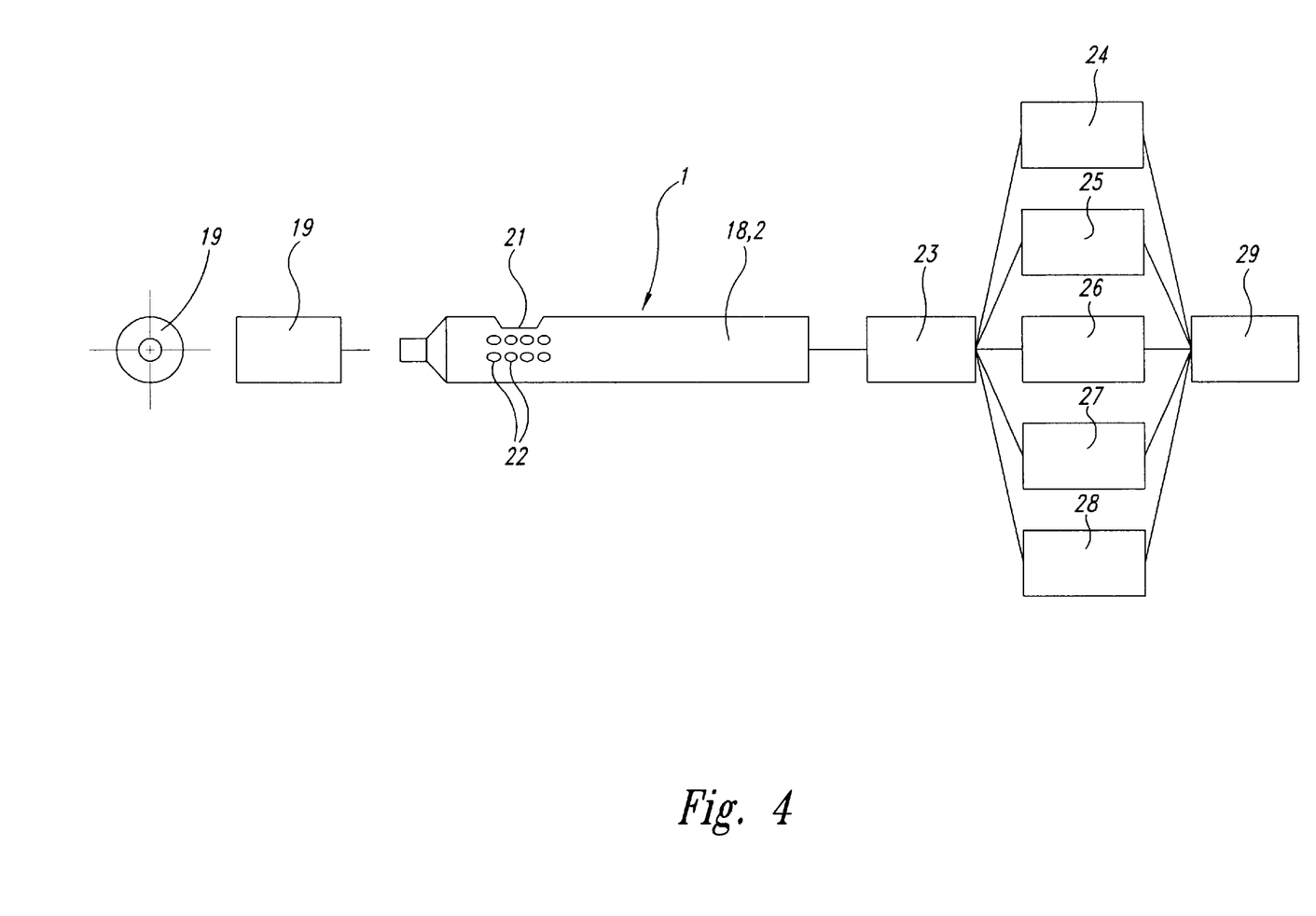
FIG. 4 is a schematic sketch showing a handle with connectable supply units for an instrument of the invention according to the first embodiment.

FIG. 4 shows a second part 18 of the carrier device 2 which is designed as a handle. The handle 18 is detachably connectable to the first part 20 via a schematically shown connection member 19. A circular hollow cross-section of the connection member 19 is also schematically illustrated at the left side.

The handle 19 has a marking 21 molded into the outside as a recess. A plurality of gripping knobs 22 are provided around the area of the marking 21.

As schematically illustrated, the instrument 1 is provided with a foot-operated switch 23 by which the tissue size-reducing device and/or the milling unit can be activated and deactivated independently of each other. The sucking function or the flushing function can possibly be activated via said switch.

A milling drive device 24, a vibration drive 25, a suction pump 26, a flushing system 27 and a light source 28 are illustrated in the manner of blocks. All of these devices can be controlled by a microprocessor 29.

The flushing system 27 may also be designed as a cooling system to cool the instrument 1 during operation.

Figure 5:
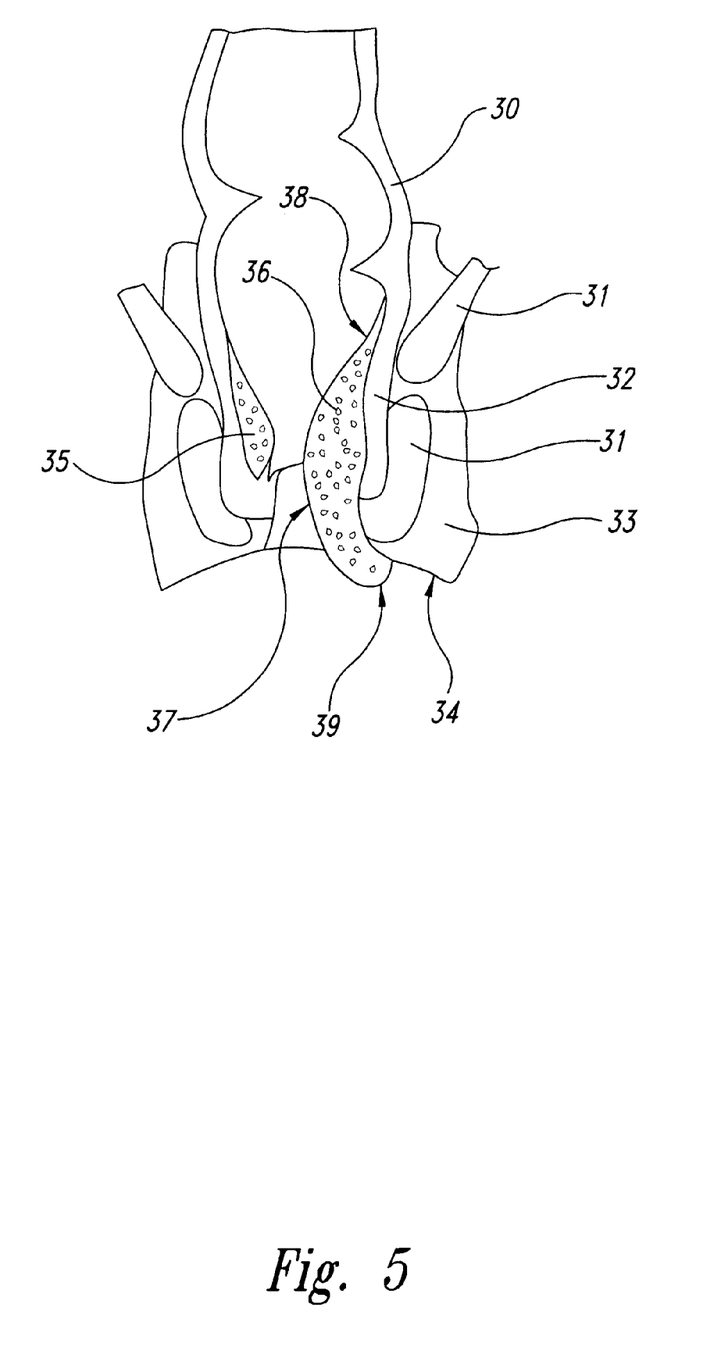
FIG. 5 is a longitudinal section through the rectal area with an enlarged hemorrhoidal complex.

FIG. 5 shows the rectal portion with the rectum 30, an outer sphincter 31, an inner sphincter 32, subcutaneous fatty tissue 33 and the outer skin 34 of a buttock. Near the anal orifice there is a hemorrhoidal complex 35 of a standard size at the left side and a hemorrhoidal complex 36 of an enlarged size at the right side, the complex 36 having an approximately fourth-degree enlargement in the illustration. The hemorrhoidal tissue 36 is located below the anoderm 37 which forms the skin between the skin of the buttock and the inner mucous membrane of the rectum. The anoderm has a great nerve density, thereby ensuring sensory continence.

When hemorrhoidal tissue is removed, the blood supply is first interrupted by ligatures on the inner layer 38 of the inner sphincter 32. A small incision is then made in the base portion 39 of the hemorrhoidal tissue near the skin 34. Thanks to said incision the instrument 1 can subanodermally be introduced into the complex 36. The incision can be made in the skin 34 or at least portionwise on the attachment portion of the anoderm 37.

First of all, only the vibrating surgical tissue-size reducing device 4 is used and the hemorrhoidal tissue is prepared and fragmented. Preferably, one proceeds along the edge of the inner sphincter 42 at the one side and directly below the anoderm 37 at the other side.

The travel of the front end portion 3 through the tissue is diaphanoscopically viewed and controlled with the aid of the light providing device 12 from the outside through the anoderm.

After preparation and fragmentation the milling unit 4 is used and the size of the hemorrhoidal tissue is reduced, the tissue being discharged with the aid of the flushing system or the suction system.

The suction system is also used for moving the tissue at a slight negative pressure to the milling unit 5 or to the tissue size-reducing device 4 to treat the tissue.

Figure 6:
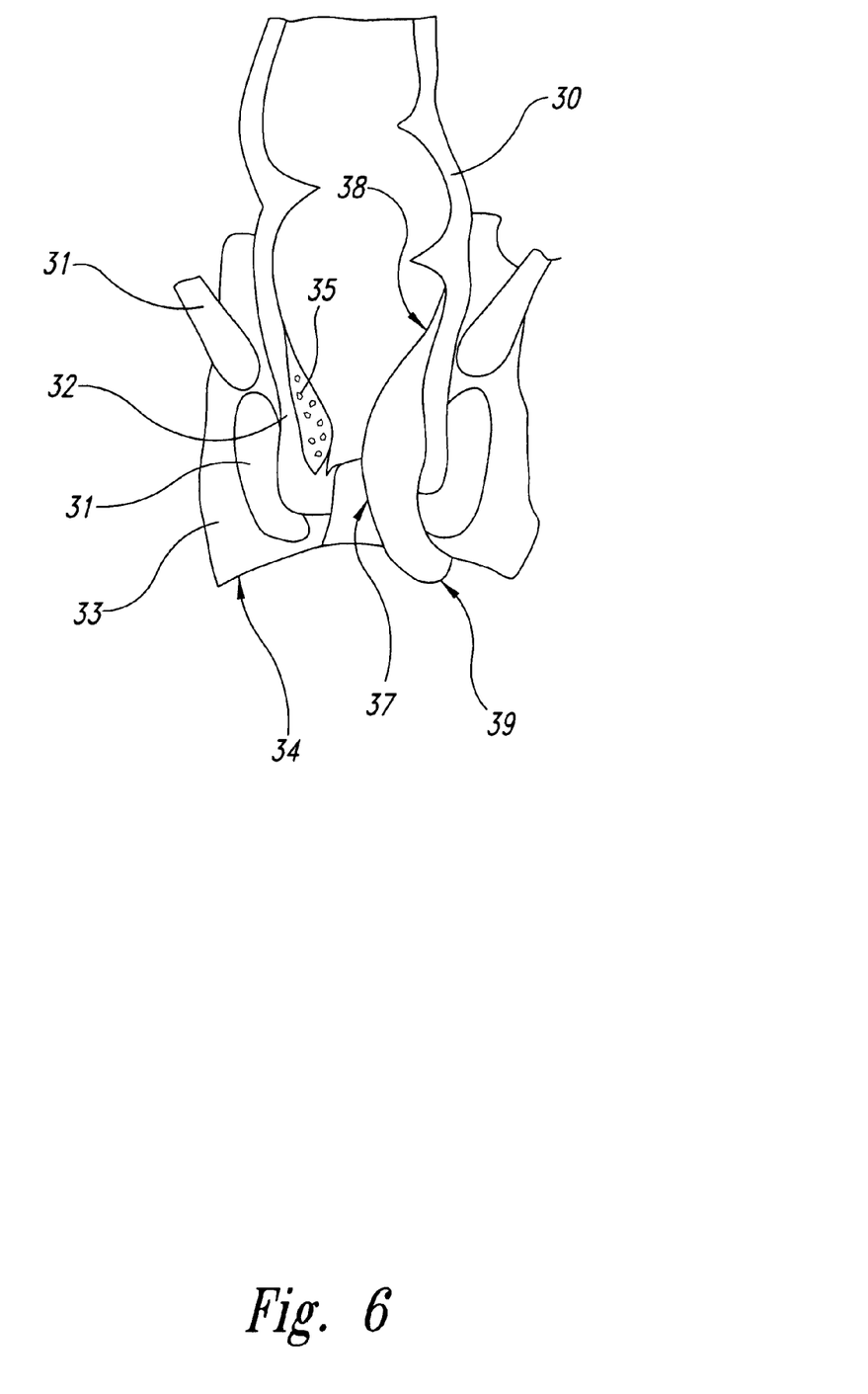
FIG. 6 is a longitudinal section through a rectal area with the hemorrhoidal complex being removed.

FIG. 6 shows the state after a complete hemorrhoidal resection. The figure shows the empty balloon-like area between anoderm and inner wall of the rectum.

Figure 7:
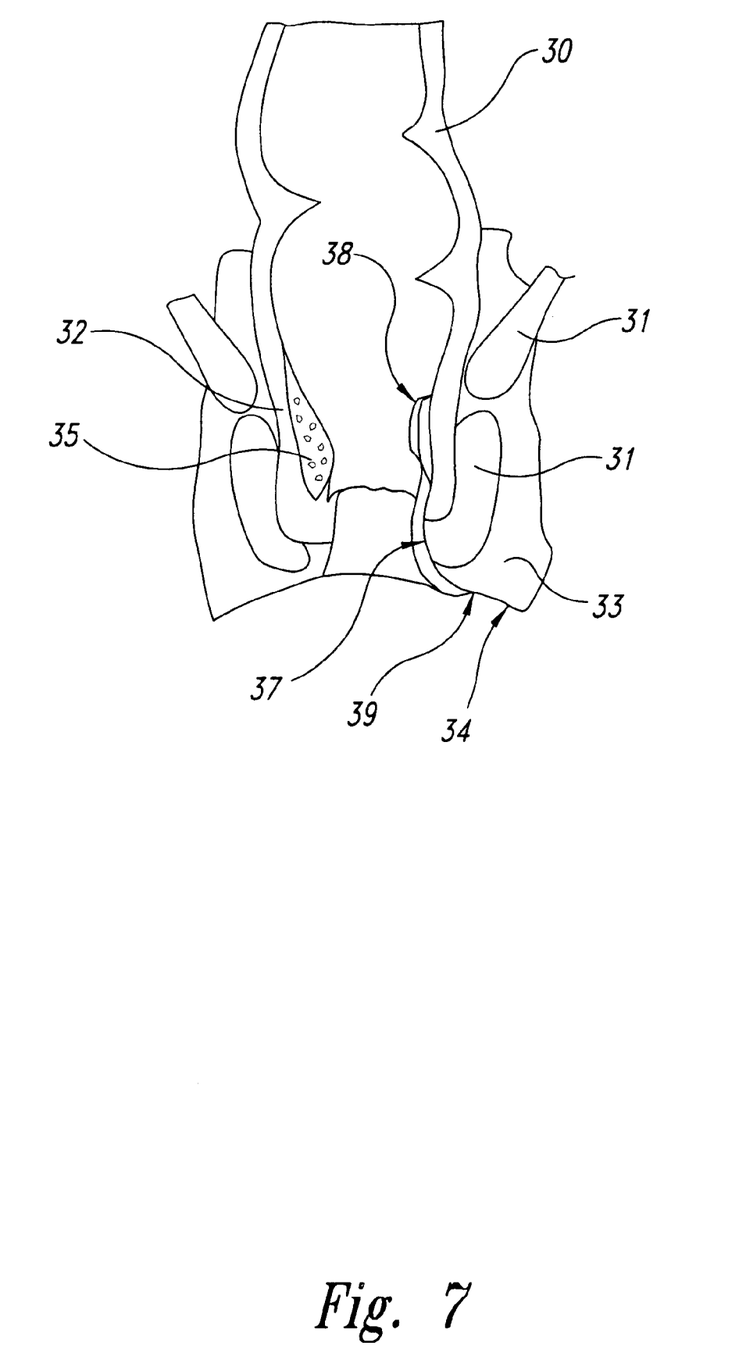
FIG. 7 is a longitudinal section through the rectum in the postoperative state.

FIG. 7 shows the postoperative state in which the anoderm is transpositioned into the anal canal in accordance with the anatomy and suitably sutured at said place. The small incision can still be used for drainage.

Advantageously, the anoderm can be maintained during surgery because the hemorrhoidal tissue can be treated subanodermally with the aid of the instrument 1.

The instrument according to the invention provides a novel surgical technique which may be designated as "minimal invasive subanodermal hemorrhoidectomy". The method and the instrument have been developed by the applicant himself. For the first time, the use of the inventive instrument permits a subanodermal resection of the hemorrhoidal plexus without incision of the anoderm, but with a subsequent transposition of the anoderm into the anal canal in accordance with anatomical conditions. The new surgical method preferably comprises the following steps:

1. Optionally, subcutaneous submucous subinjection of the hemorrhoidal node, in the case of circular hemorrhoidal prolapse, of the main segments at 3, 7 and 11 o'clock lithotomy position and possibly of the satellite node with vasoconstricting detachment with addition of a local anesthetic.
2. Inspecting and digital searching (palpable pulsations) of the Arteria rectalis sup. branches, piercing ligatures—preliminary transmucous—with anchorage of the sutures to the inner layer of the internal muscle, use is made of resorbable suture material, thickness 3×0, atraumatic, leaving the threads long and clipping the same.
3. Transverse incision of the skin at the base of the hemorrhoidal node at a length of about 0.5 to 1 cm in the area of the anal marginal ulcer.
4. Exposure and reliable identification of the edge of the Musculus sphincter internus.
5. From this section detachment of the hemorrhoidal plexuses towards the vessel base and the lateral segment boundaries, in the correct layer, directly on the edge of the M. sphincter internus and directly subanodermally, use being here made of the inventive instrument which with the aid of the ultrasonic surgical technique first isolates the hemorrhoidal plexus from the internus and from the anoderm under diaphanoscopic cold-light control; as a further step the correspondingly mobilized plexuses are resected under dosed suction using the shaver technique.

Hence, the novel method is characterized in that the instrument according to the invention is used for detachment of the hemorrhoidal plexuses, the instrument permitting the isolation of the hemorrhoidal plexus from the internus and the anoderm.

The novel method using the instrument according to the invention has the following advantages:

1. As a reconstructional surgical method, the technique is simple in comparison with the known methods, it does not require any assistance and it is less time-consuming (about a third of the surgical duration of the method according to Parks or Fangler-Arnold).
2. The highly sensitive anoderm is not incised primarily, but is nevertheless repositioned into the anal canal in accordance with the anatomy; 3 to 4 small skin incisions having a maximum length of 1 cm minimize the resulting wound surface to the "outside".
3. As a consequence, considerable reduction of the postoperative pain intensity.
4. Shortening of the hospitalization duration, possible performance of the operation on a surgical day-care basis.

Hence, for the first time the present invention discloses the use of shaver-like instruments, optionally in combination with ultrasonic surgical instruments, in the proctologic field for hemorrhoid resection. Optionally, it is also possible to use the shaver-like instrument alone with a diaphanoscopic unit.

Figure 8:
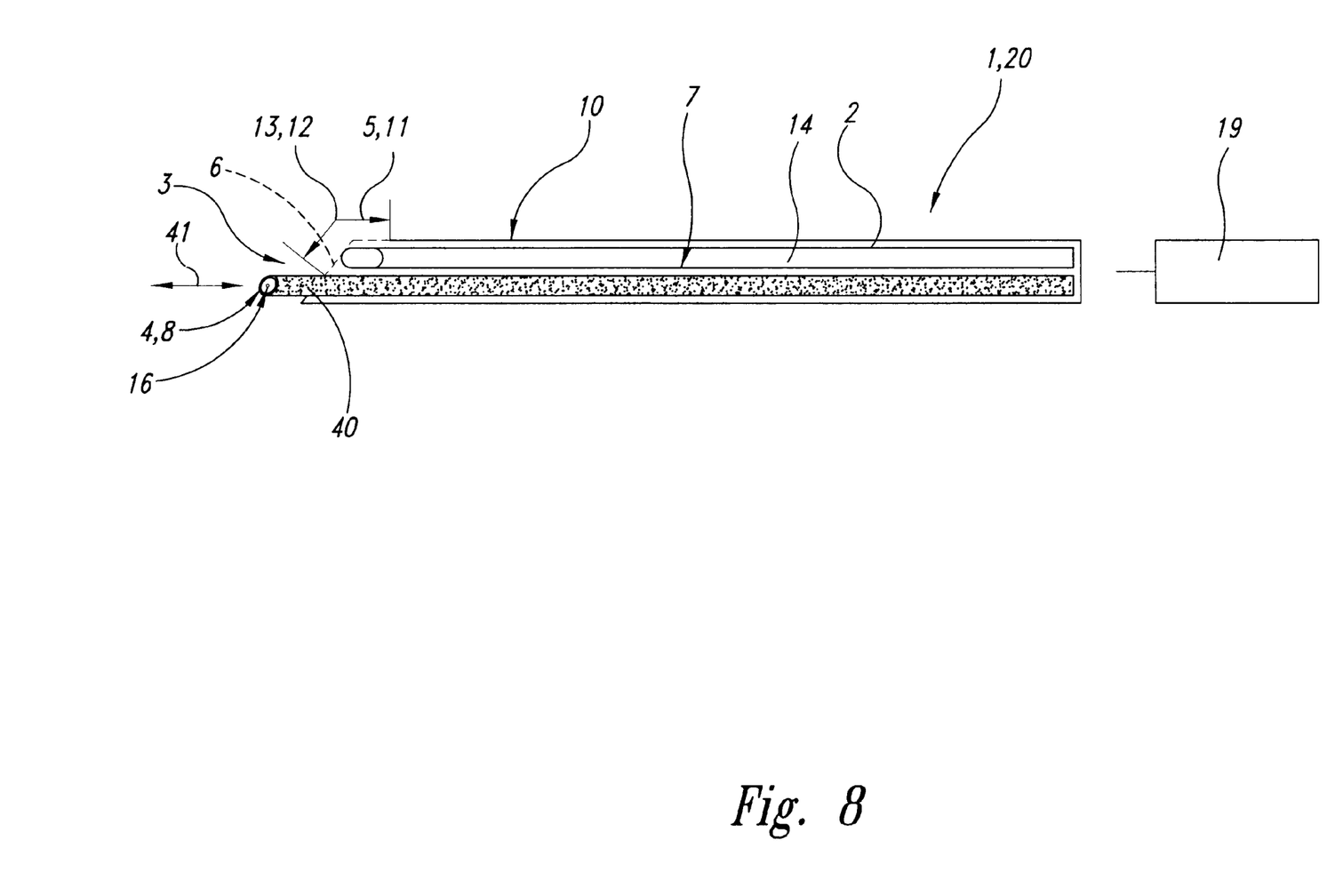
FIG. 8 is a schematic lateral view showing a first part of an instrument of the invention according to a second embodiment of the invention.

FIG. 8 schematically shows a first part 20 of a hemorrhoid resectioning instrument 1 of the invention according to a second embodiment. The second embodiment mainly differs from the first embodiment by the following points; as for the rest, reference is made to the description of the first embodiment.

The carrier device 2 is designed approximately as a sleeve or trocar in which the milling unit 5 and the tissue size-reducing device 4 are insertable either jointly or independently of each other from a rear portion into the front end portion 3. The tissue size-reducing device 4 comprises a rod-like body 40 the front end of which has arranged thereon the active surface 8. The active surface 8 is approximately circular, comprising an approximately circular suction opening 15 arranged in the center thereof. Active surface 8 and suction opening 16 are arranged in the circumferential portion of the rod-like body 40. Optionally, however, they may be provided directly on the front tip.

The rod-like body 40 is arranged in the carrier device 2 in a longitudinally displaceable manner. The direction of displacement is indicated by the directional arrow 41. FIG. 8 shows a position in which the active surface 8 is pushed out of the carrier device 2 to project therefrom approximately in the manner of a finger. Optionally, the rod-like body 40 may also be rotatable in the carrier device 2 so that it is possible to work on all sides with the active surface 8 provided in the circumferential area. A suitable opening is provided in the inclined surface 6 so as to push the rod-like body 40 beyond the inclined surface 6 in a forward direction.

Moreover, the handle 18 according to the first embodiment can of course be used for the second embodiment according to the invention.

Figure 9:
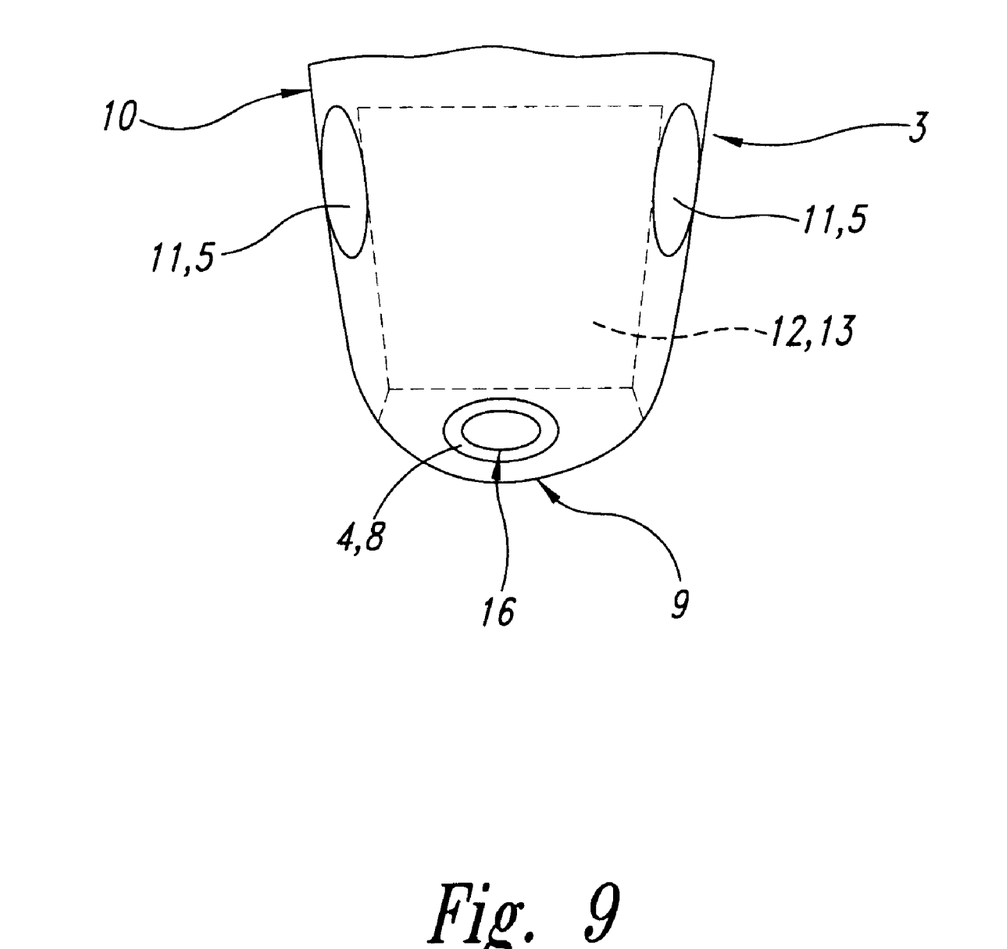
FIG. 9 is a schematic diagram showing the arrangement of the individual elements of the front end portion of an instrument of the invention according to a third embodiment of the invention.

FIG. 9 is a schematic straight top view on the inclined surface 6 according to a third embodiment of the invention. This embodiment is substantially identical with the first embodiment according to FIG. 3, so that reference is made to the corresponding description.

In the third embodiment the active surface 8 as compared with the first and second embodiments is made oval. It may e.g. be elliptical. The suction opening 16 is centrally arranged in the oval form and is also oval-shaped. With the oval shape, the planar area of the inclined surface 6 can be exploited in an improved manner in restriction to the light-providing surface area 13, resulting in a larger active surface 8 on the whole.

Of course, said oval shape may also be applied to the first and second embodiments of the invention.

What is claimed is:

1. An instrument for resectioning hemorrhoids for the minimal invasive subanodermal removal of hemorrhoidal tissue, with a narrow, elongated carrier device having a terminal tip being provided, comprising a vibrating surgical tissue size-reducing device proximate the terminal tip of the carrier device for the preparation and fragmentation of hemorrhoidal tissue, and at least one tissue-removing milling unit mounted in the carrier device.

2. The instrument according to claim 1 wherein the milling unit comprises a milling knife, which is movable in the carrier device, and insertable into the tissue.

3. The instrument according to claim 2 wherein the carrier device comprises at least one milling opening in the area of which the milling knife is arranged.

4. The instrument according to claim 2, further comprising an active surface of the tissue size-reducing device provided in a front end portion of the carrier device.

5. The instrument according to claim 2 wherein the tissue size-reducing device and the milling unit are provided on a front end portion of the carrier device.

6. The instrument according to claim 1 wherein the milling unit is spaced apart from the tip of the carrier device.

7. The instrument according to claim 6 wherein the tissue size-reducing device is arranged closer to the tip of the carrier device than the milling unit when viewed in a longitudinal direction of the carrier device.

8. The instrument according to claim 1 wherein at least two spaced-apart milling openings of the milling unit are provided.

9. The instrument according to claim 8 wherein the milling openings are arranged approximately on the same circumferential line when viewed in a direction perpendicular to a longitudinal axis of the carrier device.

10. The instrument according to claim 8, further comprising an active surface of the tissue size-reducing device provided in a front end portion of the carrier device.

11. The instrument according to claim 8 wherein the tissue size-reducing device and the milling unit are provided on a front end portion of the carrier device.

12. The instrument according to claim 1, further comprising milling openings in a lateral circumferential area of the carrier device.

13. The instrument according to claim 12 wherein the milling openings are arranged approximately on the same circumferential line when viewed in a direction perpendicular to a longitudinal axis of the carrier device.

14. The instrument according to claim 1, further comprising an active surface of the tissue size-reducing device provided in a front end portion of the carrier device.

15. The instrument according to claim 14 wherein the tissue size-reducing device is arranged closer to the tip of the carrier device than the milling unit when viewed in a longitudinal direction of the carrier device.

16. The instrument according to claim 1 wherein the tissue size-reducing device and the milling unit are provided on a front end portion of the carrier device.

17. The instrument according to claim 16 wherein the tissue size-reducing device is arranged closer to the tip of the carrier device than the milling unit when viewed in a longitudinal direction of the carrier device.

18. The instrument according to claim 1 wherein the tissue size-reducing device is arranged closer to the tip of the carrier device than the milling unit when viewed in a longitudinal direction of the carrier device.

19. The instrument according to claim 1 wherein the tissue size-reducing device is arranged directly at a foremost tip of the carrier device.

20. The instrument according to claim 1 wherein a front end portion has an inclined surface extending at an angle relative to a longitudinal axis of the carrier device, resulting in the formation of the front end portion having an approximately wedge-shaped or beak-shaped cross-section.

21. The instrument according to claim 20 wherein the angle of inclination of the inclined surface relative to the longitudinal axis of the carrier device is about 400° to 500.

22. The instrument according to claim 20 wherein an active surface of the tissue size-reducing device is at least partially integrated into the inclined surface.

23. The instrument according to claim 1, further comprising a light providing device for emitting diaphanoscopically usable light.

24. The instrument according to claim 23 wherein the light providing device is disposed approximately in the surface area between the tissue size-reducing device and the milling units.

25. The instrument according to claim 23 wherein the light providing device is disposed in an inclined surface extending at an angle relative to a longitudinal axis of the carrier device.

26. The instrument according to claim 23 wherein the light providing device is provided in a circumferential area near the milling unit.

27. The instrument according to claim 23 wherein the light providing device has a large-surface light-emitting surface relative to active surfaces of milling unit and/or tissue size-reducing device.

28. The instrument according to claim 1, further comprising at least one suction channel which is connectable to a vacuum pump and terminates in a suction opening of the carrier device.

29. The instrument according to claim 28 wherein the suction opening is centrally provided in an active surface of the tissue size-reducing device.

30. The instrument according to claim 28 wherein milling opening/milling openings is/are formed as a suction opening in a circumferential area of the carrier device, with a milling knife that is movable in the carrier device being provided in the area thereof.

31. The instrument according to claim 1, further comprising at least one flushing channel which is connectable to a flushing system and terminates in a flushing opening provided in a front end portion.

32. The instrument according to claim 31 wherein milling opening/milling openings is/are formed as a flushing opening in a circumferential area of the carrier device, with a milling knife that is movable in the carrier device being provided in the area thereof.

33. The instrument according to claim 31 wherein the flushing opening is centrally provided in an active surface of the tissue size-reducing device.

34. The instrument according to claim 1 wherein the carrier device comprises a first part carrying a front end portion and a second part which is detachably connectable to said first part and designed as a handle.

35. The instrument according to claim 1, further comprising a handle of the carrier device having a marking indicative of the angular orientation of the end portion relative to a longitudinal axis of the carrier device.

36. The instrument according to claim 1 wherein the tissue size-reducing device and the milling unit are operable independently of each other.

37. The instrument according to claim 1 wherein the carrier device has a hollow cross-section through which the milling unit and the tissue size-reducing device can be supplied.

38. The instrument according to claim 1 wherein the tissue size-reducing device and/or the milling unit is/are supported in the carrier device to be longitudinally displaceable.

39. The instrument according to claim 1 wherein an active surface of the tissue size-reducing device can be pushed out of the carrier device into a position in which the active surface projects forwards from the carrier device.

40. The instrument according to claim 1 wherein an active surface of the tissue size-reducing device has an approximately oval or circular shape.

41. The instrument according to claim 1 wherein the tissue size-reducing device is arranged closer to the tip of the carrier device than the milling unit when viewed in a longitudinal direction of the carrier device.

42. A medical instrument for resectioning vascular tissue, the instrument comprising:
an elongated carrier device having a terminal tip;
a vibrating surgical tissue size-reducing device proximate the terminal tip of the carrier device; and
at least one tissue-removing milling unit mounted in the carrier device.

43. The instrument of claim 42 wherein the milling unit comprises a milling knife which is movable in the carrier device.

44. The instrument of claim 42 wherein the tissue size-reducing device comprises an ultrasonic surgical tool.

45. The instrument of claim 42 wherein the tissue size-reducing device is moveably disposed in the carrier tip to permit extension of an active surface of the tissue size-reducing device beyond the terminal tip of the carrier device.

* * * * *